United States Patent [19]

Bernstein

[11] Patent Number: 6,048,851

[45] Date of Patent: *Apr. 11, 2000

[54] SOLID PHARMACEUTICAL COMPOSITIONS FOR THE ORAL ADMINISTRATION OF GALLIUM

[76] Inventor: Lawrence Richard Bernstein, 380 Willow Rd., Menlo Park, Calif. 94025

[*] Notice: This patent is subject to a terminal disclaimer.

[21] Appl. No.: 09/015,425

[22] Filed: Jan. 29, 1998

Related U.S. Application Data

[62] Division of application No. 08/956,175, Oct. 22, 1997, which is a continuation of application No. 08/655,220, Jun. 5, 1996, abandoned, which is a continuation of application No. 08/505,037, Jul. 21, 1995, Pat. No. 5,574,027, which is a continuation of application No. 08/309,624, Sep. 21, 1994, abandoned, which is a continuation of application No. 08/104,623, Aug. 11, 1993, abandoned, which is a continuation of application No. 07/782,434, Oct. 25, 1991, Pat. No. 5,258,376, and a continuation-in-part of application No. 07/656,016, Feb. 14, 1991, abandoned, which is a continuation of application No. 07/440,277, Nov. 22, 1989, abandoned.

[51] Int. Cl.⁷ .................................................. A61K 31/555
[52] U.S. Cl. ............................ 514/184; 549/210
[58] Field of Search .............................. 514/184; 549/210

[56] References Cited

U.S. PATENT DOCUMENTS

| | | |
|---|---|---|
| 2,460,188 | 1/1949 | O'Kane . |
| 3,799,945 | 3/1974 | D'Amico . |
| 3,927,195 | 12/1975 | Messora . |
| 4,529,593 | 7/1985 | Warrell et al. . |
| 4,575,502 | 3/1986 | Hider et al. . |
| 4,596,710 | 6/1986 | Collery . |
| 4,665,064 | 5/1987 | Hider et al. . |
| 4,686,104 | 8/1987 | Bockman et al. . |
| 4,704,277 | 11/1987 | Bockman et al. . |
| 5,175,006 | 12/1992 | Matkovic et al. . |
| 5,177,068 | 1/1993 | Callingham et al. . |

FOREIGN PATENT DOCUMENTS

| | | |
|---|---|---|
| 2242191 | 9/1991 | United Kingdom . |
| WO 89/01475 | 2/1989 | WIPO . |
| WO 91/17751 | 11/1991 | WIPO . |

OTHER PUBLICATIONS

Adamson et al. (1975), "Studies on the Antitumor Activity of Gallium Nitrate (NSC–15200) and Other Group IIIa Metal Salts," *Cancer Chemotherapy Reports*, Part 1, 59(3):599–610.

Barr et al. (1986), "Effects of the Pyrones, Maltol and Ethyl Maltol, on Iron Absorption from the Rat Small Intestine," *J. Pharm. Pharmacol.* 39:203–211.

Bockman et al. (1983), "Abstracts: Bone Metabolism and Cell Biology," *Calcified Tissue International* 35(4–5):637.

Farrar et al. (1988), "Tissue Distribution of Gallium Following Administration of the Gallium–Maltol Complex in the Rat," *Food Chem. Toxic.* 26:523–525.

Finnegan et al. (1987), "Neutral Water–Soluble Post–Transition Metal . . . ," *Inorganic Chemistry* 26:2171–2176.

Foster et al. (1986), "Gallium Nitrate: The Second Metal with Clinical Activity," *Cancer Treatment Reports* 70(11):1311–1318.

Hart et al. (1971), "Antitumor Activity and Toxicity of Salts of Inorganic Group IIIa Metals:Aluminum, Gallium, Indium, and Thallium," *Proc. Natl. Acad. Sci. USA* 68(7):1623–1626.

Warrell et al., (1989) "Gallium in the Treatment of Hypercalcemia and Bone Metastasis," *Important Advances in Oncology*, chapter 12 (Philadelphia: J.B. Lippincott Company).

*Primary Examiner*—Keith D. MacMillan
*Attorney, Agent, or Firm*—Dianne E. Reed; Reed & Associates

[57] ABSTRACT

The subjects of this invention are pharmaceutical compositions that comprise gallium complexes of 3-hydroxy-4-pyrones. The compositions have been developed to provide pharmaceutically acceptable gallium bioavailability together with low toxicity, particularly for oral administration. Compositions included in this invention should be useful in providing gallium to humans and other animals for a wide variety of medical and veterinary applications, including the treatment, prevention, or diagnosis of certain bone diseases, certain cancers, and certain disorders of calcium homeostasis.

11 Claims, 1 Drawing Sheet

Figure 1. Results of preliminary gallium bioavailability study on gallium ethyl maltol complex.
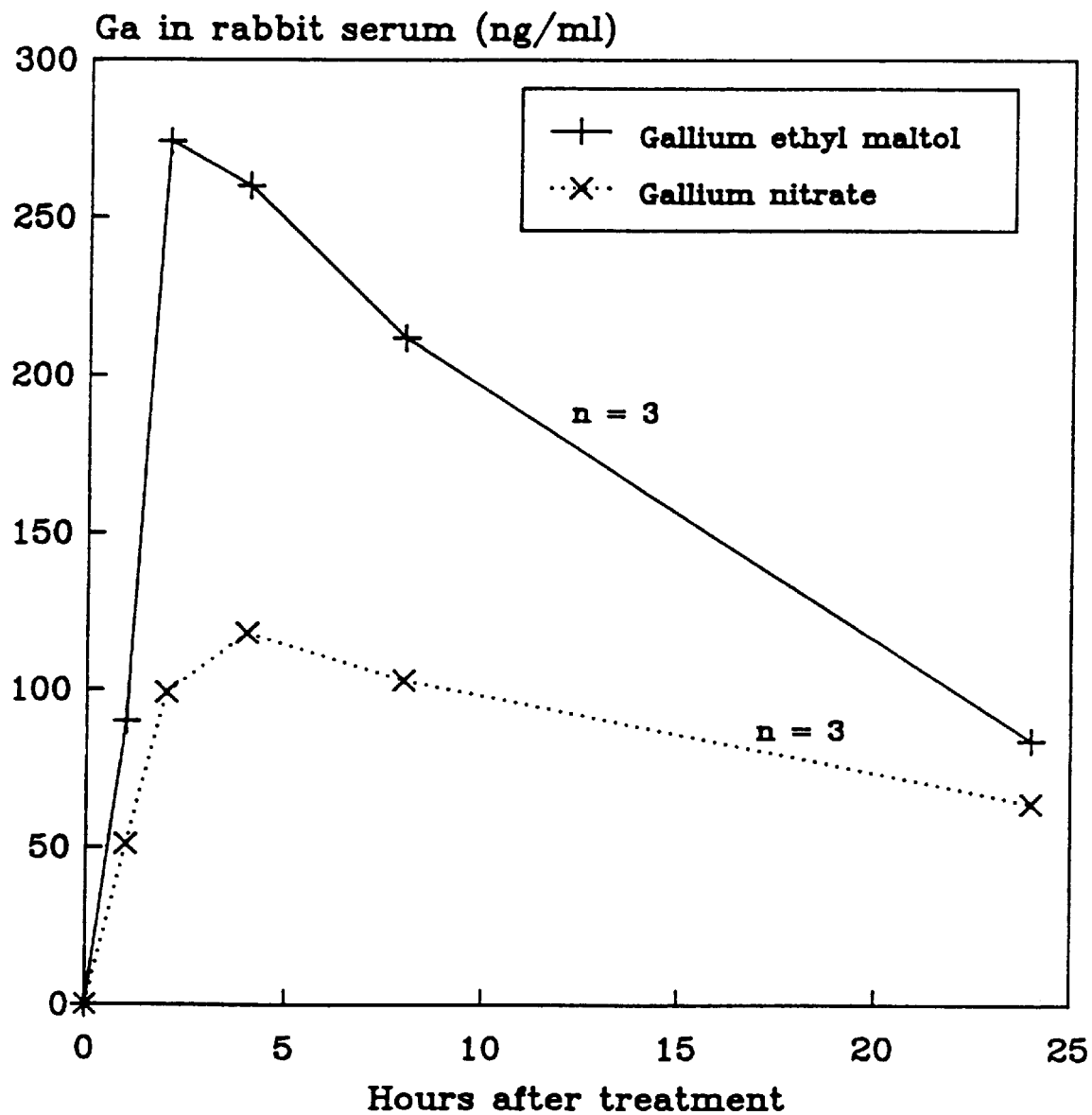

6,048,851

SOLID PHARMACEUTICAL COMPOSITIONS FOR THE ORAL ADMINISTRATION OF GALLIUM

CROSS-REFERENCE TO RELATED APPLICATIONS

This is a divisional of U.S. Ser. No. 08/956,175, filed Oct. 22, 1997, allowed, which was a continuation of U.S. Ser. No. 08/655,220, filed Jun. 5, 1996, abandoned, which was a continuation of U.S. Ser. No. 08/505,037, filed Jul. 21, 1995, now issued as U.S. Pat. No. 5,574,027, which was a continuation of U.S. Ser. No. 08/309,624, filed Sep. 21, 1994, abandoned, which was a continuation of U.S. Ser. No. 08/104,623, filed Aug. 11, 1993, abandoned, which was a continuation of Ser. No. 07/782,434, filed Oct. 25, 1991, now issued as U.S. Pat. No. 5,258,376, which was a continuation-in-part of U.S. Ser. No. 07/656,016, filed Feb. 14, 1991, abandoned, which was a continuation of Ser. No. 07/440,277, filed Nov. 22, 1989, abandoned.

References Cited

U.S. PATENT DOCUMENTS

| | | | |
|---|---|---|---|
| 4,529,593 | 7/1985 | Warrell et al. | 424/127 |
| 4,575,502 | 3/1986 | Hider et al. | 514/184, 814 |
| 4,596,710 | 6/1986 | Collery | 424/131 |
| 4,704,277 | 11/1987 | Bockman et al. | 424/127, 131; 514/492 |

OTHER PUBLICATIONS

Adamson, R. H., Cannellos, G. P., and Sieber, S. M., 1975, Studies on the antitumor activity of gallium nitrate (NSC-15200) and other group IIIa metal salts. Cancer Chemotherapy Reports, v. 59, p. 599–610.

Hart, M. M. and Adamson, R. H., 1971, Antitumor activity and toxicity of salts of inorganic group IIIa metals: aluminum, gallium, indium, and thallium. Proceedings of the National Academy of Sciences U.S.A., v. 68, p. 1623–1626.

Windholz, M., Budavari, S., Stroumtsos, L. Y., and Fertig, M. N., 1976, The Merck Index, ninth edition, p. 741–742. Rahway, N.J. Merck and Company.

FIELD OF THE INVENTION

The invention comprises gallium compositions for pharmaceutical use. These compositions provide pharmaceutically acceptable gallium bioavailability, and are particularly useful for oral administration. Gallium is potentially of great pharmaceutical value for the treatment and prevention of many human and animal diseases, including hypercalcemia, cancer, and especially certain widespread degenerative bone diseases such as osteoporosis and Paget's disease.

BACKGROUND

Gallium is known to accumulate in certain tumors, inflamed tissue, and bone tissue by mechanisms that are largely unknown. Binding of gallium to transferring, particularly lactoferrin, is thought to be responsible for some of the transport of gallium in the body, and for the concentration of gallium in certain tumors and inflamed tissues. Radioactive $^{67}$gallium citrate compositions are used in patients to diagnose certain malignancies and infections, including those in bone tissue. Non-radioactive gallium compositions, and compositions containing other Group IIIa elements, have been found effective in treating some tumors in animals and humans. Gallium is thought to be the least toxic and most effective of these Group IIIa elements (Hart and Adamson, 1971). U.S. Pat. No. 4,596,710 discloses an anticancer treatment that uses gallium chloride. The gallium ion itself appears to be the active agent; the form in which the gallium is administered (e.g. as the nitrate, sulfate, or chloride) does not appear to affect its activity (Adamson et al., 1975).

Gallium appears particularly promising for treating and preventing hypercalcemia and certain bone diseases. Treatable bone diseases include such widespread conditions as osteoporosis, osteopenia, Paget's disease, malignant bone disease, and other conditions associated with increased bone resorption in humans or animals. U.S. Pat. Nos. 4,529,593 and 4,704,277 disclose treatments using gallium salts, preferably gallium nitrate, for regulating the resorption of calcium from bone in certain bone diseases and hypercalcemia, and for increasing the mass and tensile strength of bone.

If gallium is to be used as a treatment for widespread, chronic conditions such as osteoporosis (which affects over twenty million people in the United States), an oral form of gallium is needed that is safe and has high bioavailability. The currently preferred form of gallium (a composition containing mostly gallium nitrate) is absorbed from the gastrointestinal tract of dogs into blood serum in the amount of only 0.5–2% from an orally administered dose (U.S. Pat. No. 4,529,593). The percent absorption from other simple gallium salts is not likely to be significantly different, as such salts dissociate in aqueous solutions to produce mainly trivalent gallium ions, which appear to have very low absorbability from mammalian gastrointestinal tracts. The very low observed bioavailability may not be acceptable for an orally administered drug.

The compositions included in this invention were developed to provide sufficiently high gallium bioavailabilities, especially when administered orally, to be pharmaceutically acceptable for providing gallium to humans and animals.

SUMMARY OF INVENTION

The subjects of this invention are pharmaceutical compositions that comprise gallium complexes of 3-hydroxy-4-pyrones, and some methods for producing them. The invention is designed to provide pharmaceutically acceptable gallium bioavailability with low toxicity, particularly for oral administration. Compositions included in this invention should be useful in providing gallium to humans and other animals for a wide variety of medical and veterinary applications, including the treatment, prevention, or diagnosis of certain bone diseases, certain cancers, and certain disorders of calcium homeostasis.

BRIEF DESCRIPTION OF THE FIGURE

FIG. 1 is a graphical representation of the data given in Table 1, showing a comparison of the absorption of gallium into blood serum from gallium ethyl maltol suspension versus gallium nitrate solution, by oral administration to rabbits. Details of the experiment are given in the section entitled Example 2, which follows. Due to uncertainties in the measurement of gallium in serum, the relative proportions of gallium in the samples are more significant than the measured concentration values themselves.

DETAILED DESCRIPTION OF THE PREFERRED EMBODIMENTS

The following particulars of the invention describe some preferred aspects thereof. These particulars, however, do not indicate any limitations to the invention, but are only examples of particular, preferred embodiments.

The invention comprises any and all pharmaceutical compositions that comprise a gallium complex or gallium complexes of 3-hydroxy-4-pyrone wherein from none through three of the hydrogen atoms attached to ring carbon atoms are replaced by a hydrocarbon group of from one through six carbon atoms. Such complexes, and the crystalline and non-crystalline solids and fluids, including solutions, that contain them are believed to be wholly new, as no prior reference to them can be found. Such complexes are, however, believed to be analogous in many respects to similar complexes of iron, as described, for example, in U.S. Pat. No. 4,575,502. It is noted that very few gallium analogs of iron compounds are known. Some of the iron complexes are reported to provide high oral bioavailability of iron, and some are used as dyes (U.S. Pat. No. 4,575,502).

The unsubstituted form of 3-hydroxy-4-pyrone (also called pyromeconic acid) contains three hydrogen atoms that are bound only to ring carbon atoms (Formula 1). Any combination of these Formula 1
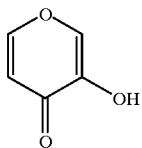

Formula 2
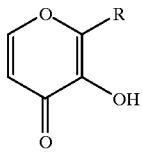

Formula 3
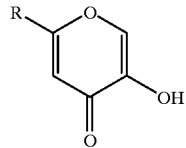

Formula 4
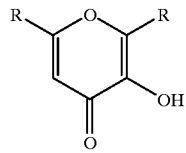

Formula 5
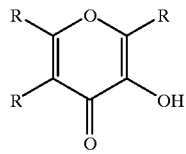

three hydrogen atoms can be replaced by a hydrocarbon group; all such substituted compositions are included in the invention. The locations of a few possible substitutions are presented in Formulas 2–5, in which R is a hydrocarbon group (including ethyl, methyl, isopropyl, and n-propyl groups); many others are also possible. The hydrocarbon groups are preferably acyclic and are preferably unbranched. Groups containing six or fewer carbon atoms, particularly of one through three carbon atoms, especially methyl or ethyl, are preferred. One substitution is preferred; a substitution at either the 6-position or especially the 2-position is preferred. Some examples of specific compounds whose gallium complexes may be used in compositions comprised by the invention are: 3-hydroxy-2-methyl-4-pyrone (Formula 2, $R=CH_3$; also called maltol, larixinic acid) and 3-hydroxy-2-ethyl-4-pyrone (Formula 2, $R=C_2H_5$; also called ethyl maltol, ethylpyromeconic acid), both of which are of the most interest; 3-hydroxy-4-pyrone (Formula 1; also called pyromeconic acid); and 3-hydroxy-6-methyl-4-pyrone (Formula 3, $R=CH_3$). The neutral complex of hydroxypyrone:gallium in 3:1 molar proportion is preferred.

This invention includes methods for the preparation of gallium complexes of 3-hydroxy-4-pyrone or 3-hydroxy-4-pyrones wherein from one through three of the hydrogen atoms attached to ring carbon atoms are replaced by a hydrocarbon group containing from one through six carbon atoms. Such methods comprise reacting such hydroxypyrones with gallium ions and isolating, at least in part, the resulting complex or complexes.

Certain of the 3-hydroxy-4-pyrones occur naturally and may be obtained by extraction from the natural sources. For example, maltol is found in the bark of the young larch tree (*Larix decidua* Mill.), and in pine needles, chicory, wood tars and oils, and roasted malt (Windholz et al., 1976). Certain of the 3-hydroxy-4-pyrones are available commercially, including maltol and ethyl maltol. Others can be made from pyromeconic acid as a starting material, which can be derived from the decarboxylation of meconic acid. It is noted that maltol and ethyl maltol are in widespread use as flavoring and fragrance-enhancing agents for foods, and have very low toxicities when taken orally.

The gallium complexes can be prepared by the reaction of gallium ions and 3-hydroxy-4-pyrones in solution. Gallium ions can be derived from a gallium salt, such as a gallium halide, particularly gallium chloride, or a gallium nitrate compound, especially a hydrated gallium nitrate. The gallium nitrate compounds are often preferable as they are easier to work with than gallium halides, which may be highly irritating and may react violently with many solvents, including water. Using the proper safeguards, a variety of gallium salts can be used. The reaction is conveniently effected in a mutual solvent, including but not limited to mixtures containing water, ethanol, methanol, and chloroform. Pure water may be used in many cases, though the purification of the gallium hydroxypyrone complexes may be difficult if it is used. A preferable method, if it is desired to separate at least a major part of reaction by-products such as sodium nitrates, sodium chloride, and sodium carbonates, is to use a mixture containing roughly equal parts of ethanol and chloroform, with a trace of water. The reaction by-products mentioned above have very low solubilities in this mixture and can be removed readily by filtration.

To produce the preferred neutral 3:1 hydroxypyrone:gallium complex, the hydroxypyrone and the gallium ions are mixed in 3:1 molar proportions, preferably with a slight excess of hydroxypyrone to insure a great preponderance of the 3:1 complex over the 2:1 and 1:1 complexes. The proportions of the particular complexes formed are dependent upon the pH of the solution. When a gallium salt such as a halide or nitrate is dissolved, the resulting solution will generally have a low pH. To form a preponderance of the preferred neutral 3:1 complex, a pH of from 5 to 10, preferably 7 through 8, is used. If a more acidic solution is used, a preponderance of the less preferred 2:1 and 1:1 complexes will instead be formed, even if a large excess of hydroxypyrone is present. Under highly basic conditions, poorly soluble gallium hydroxides may precipitate. It is preferable to regulate the pH with materials other than hydroxides such as sodium hydroxide, as the use of such hydroxides may cause the precipitation of poorly soluble gallium hydroxides, which are not wanted, and the pH may actually be buffered at a low level by this precipitation. The use of a carbonate, especially sodium carbonate, is preferred to regulate the pH. The use of sodium carbonate in a solvent mixture containing ethanol and chloroform, for example, can result in the precipitation of sodium nitrates that are very slightly soluble in this mixture, and which can be filtered off if desired to help purify the solution containing the desired pharmaceutical compositions.

The reaction to form the hydroxypyrone-gallium complex in solution is generally complete within about five minutes at about 20° C. Gentle stirring or other agitation of the solution promotes a uniform, rapid reaction. Longer reaction times may be used if found necessary. Following the separation, if desired, of reaction by-products such as sodium nitrates, sodium chloride, and sodium carbonates (depending on the solvents and reactants used), the reaction mixture may be evaporated slowly in air or, more rapidly, through the use of a rotary evaporator or by freeze drying, as examples. After drying, the gallium complex or complexes will remain in solid form. Recrystallization can be accomplished, if desired, using a suitable solvent, including but not limited to chloroform, alcohols such as ethanol and methanol, ether, water, acetone, and mixtures containing such solvents. Suitable solvents will depend upon which particular gallium complex(es) and impurities are present, upon the impurities to be separated, and upon the temperature and other physical conditions.

It is noted that the mentioned methods are not the only ones that can produce hydroxypyrones and gallium complexes with hydroxypyrones and that various alternative methods may be used as will be apparent to those skilled in the art.

The fluids in mammalian stomachs are generally at a pH below 4, which may cause the less absorbable 2:1 and 1:1 complexes, together with free hydroxypyrone, to predominate when the 3:1 complex reaches the stomach. This situation can be counteracted in several ways, a few of which are mentioned here. One possibility is to mix the 3:1 complex with a suitable buffering agent. Another possibility is to mix the 3:1 complex with an excess of free hydroxypyrone (or a salt thereof containing a physiologically acceptable cation), particularly the one used to make the 3:1 complex. Such a mixture, when dissolved in the stomach, can have the effect of shifting the equilibrium among the 1:1, 2:1, and 3:1 complexes towards a preponderance of the 3:1 complex. Another possibility is formulating or packaging the 3:1 complex in such a way that the dissociation of the 3:1 complex is prevented until the basic conditions of the small intestine are reached. Specific methods include, for example: (1) encapsulating the 3:1 complex in a material that does not dissolve until the small intestine is reached, and (2) formulating the 3:1 complex with certain gels or with other materials that greatly slow the release of the 3:1 complex.

When used for oral administration, the gallium complex may be formulated in a variety of ways. It will preferably be in solid form, and may conveniently be used in compositions containing conventional solid carriers such as lactose, starch, or dextrin, and conveniently presented in tablet or capsule form. Materials and methods to enhance gallium absorption, including those mentioned in the preceding paragraph, may be incorporated. Compositions including a liquid carrier may also be employed for oral administration. To obtain physiologically active gallium levels in the body, compositions for oral administration will likely contain between 0.01 and 20 weight percent gallium complexed with hydroxypyrone in the composition, most likely between 0.5 and 15 weight percent; experiments will be needed to obtain the suitable concentrations for particular applications.

Formulations may also be considered for other modes of administration, for example per rectum, transdermally, and by intravenous, subcutaneous, and intramuscular injection. These formulations may contain a liquid carrier that may be oily, aqueous, emulsified, or contain certain solvents suitable to the mode of administration. Compositions may be formulated in unit dose form, or in multiple or sub-unit doses. The dosage will depend on the medical application, and must be determined by suitable experiments. The compositions will likely contain between 0.001 and 15 weight percent gallium complexed with hydroxypyrone in the composition; experiments will be needed to obtain the suitable concentration for particular applications.

Formulations may also be produced that contain active ingredients other than the gallium complexes. These may include other agents to regulate calcium resorption from bone, for example, but other active agents may also be incorporated.

EXAMPLES

Example 1

Preparation of Gallium Ethyl Maltol

A 1.5M solution of ethyl maltol in chloroform is mixed with an equal volume of a 0.5M solution of gallium nitrate nonohydrate in ethanol to provide a 3:1 molar ratio of ethyl maltol to gallium ions in the mixture. The mixture is stirred for 7 minutes at 22° C. Solid anhydrous sodium carbonate is then added in a 10 molar excess, and stirring continues for an additional ten minutes. When the sodium carbonate is added, a trace of water may sometimes need to be added to facilitate the reaction, which is evidenced by some effervescence. The mixture is then filtered and the filtrate evaporated to give the solid 3:1 complex of ethyl maltol and gallium.

The complex as so produced contains 14.3(1) weight percent gallium by x-ray fluorescence analysis, as predicted for $Ga(C_7H_6O_3)_3$. The material forms white to pale beige monoclinic crystals with unit cell parameters of about a=7.899(1)A, b=8.765(1)A, c=31.626(2)A, beta=103.253(7) degrees, V=2131 $A^3$, based on powder x-ray diffraction analysis. Crystallization from other solvents or under other conditions may produce other crystal structures.

Example 2

Preliminary Bioavailability Study in Rabbits

As a preliminary test of the oral bioavailability of the 3:1 ethyl maltol:gallium complex, the complex was given to rabbits and compared to a solution of gallium nitrate. Six female New Zealand white rabbits weighing between 2.68 and 2.91 kg were used, and were not fed for 18 hours before starting the experiment. A suspension of the 3:1 gallium ethyl maltol complex in double distilled water was prepared with a concentration of 10 mg elemental gallium per 4 ml of suspension. A solution of gallium nitrate nonohydrate dissolved in double distilled water was also prepared, which had a concentration of 10 mg elemental gallium per 4 ml of solution. A small amount of solid sodium carbonate was added to the latter solution to bring the pH up to about 6. Each of the two solutions was given to three rabbits by oral gavage (through a tube inserted through the mouth to the stomach) in the amount of 4 ml per kg of body weight, equivalent to 10 mg of elemental gallium per kg of body weight. The stomach tubes were flushed by three ml of water following administration of the solutions.

Six ml of blood was taken from each rabbit at 1 hr, 2 hr, 4 hr, 8 hr, and 24 hr following administration of the solutions, and the serum separated and frozen. Control samples of blood were taken 24 hours earlier. The frozen serum samples were then sent to an independent testing laboratory for determination of the gallium contents by graphite furnace atomic absorption analysis. The testing laboratory received numbered serum samples, and never had any knowledge of the experimental conditions used to produce the samples. The results of the analyses are indicated in Table 1 and on FIG. 1. Due to uncertainties in the analytical procedures for gallium in serum, the relative proportions of gallium in the serum samples are considered more significant than the actual reported concentrations.

TABLE 1

Mean gallium content of rabbit serum (ng/ml).

|  | Gallium ethyl maltol suspension (3 animals) | Gallium nitrate solution (3 animals) |
| --- | --- | --- |
| pre-treatment | 0 | 0 |
| 1 hour | 90 | 51 |
| 2 hours | 274 | 99 |
| 4 hours | 260 | 118 |
| 8 hours | 212 | 103 |
| 24 hours | 84 | 64 |

It is seen from Table 1 and FIG. 1 that the gallium ethyl maltol suspension was absorbed in significantly higher amounts than the gallium nitrate suspension of equal volume and gallium concentration. It is important to note that no attempt was made to counteract the adverse effects of the 3:1 gallium ethyl maltol complex being exposed to the acidic conditions of the stomach. This preliminary study should therefore be considered to give a minimal value for the oral bioavailability of the gallium ethyl maltol complex compared to gallium nitrate.

I claim:

1. A pharmaceutical composition for oral administration to a human individual, comprising, in a solid dosage form, approximately 0.9 to 1800 mg of a neutral 3:1 hydroxypyrone:gallium complex in which the hydroxypyrone is either unsubstituted or substituted with one to three lower alkyl substituents, a pharmaceutically inert carrier suitable for oral drug administration, and, optionally, an additional active agent.

2. The pharmaceutical composition of claim 1 wherein an additional active agent is present.

3. The pharmaceutical composition of claim 2, wherein the additional active agent is effective to regulate calcium resorption from bone.

4. The pharmaceutical composition of claim 1, comprising approximately 9 to 360 mg of the neutral 3:1 hydroxypyrone:gallium complex.

5. The pharmaceutical composition of claim 2, comprising approximately 9 to 360 mg of the neutral 3:1 hydroxypyrone:gallium complex.

6. The pharmaceutical composition of claim 3, comprising approximately 9 to 360 mg of the neutral 3:1 hydroxypyrone:gallium complex.

7. A pharmaceutical composition for oral administration to a human individual, comprising, in a solid dosage form, approximately 0.9 to 1800 mg of a neutral 3:1 hydroxypyrone:gallium complex in which the hydroxypyrone is selected from the group consisting of 3-hydroxy-4-pyrone, 3-hydroxy-2-methyl-4-pyrone, 3-hydroxy-2-ethyl-4-pyrone, and 3-hydroxy-6-methyl-4-pyrone, a pharmaceutically inert carrier suitable for oral drug administration, and an additional active agent effective to regulate calcium resorption from bone.

8. The pharmaceutical composition of claim 7, wherein the hydroxypyrone is selected from the group consisting of 3-hydroxy-2-methyl4-pyrone and 3-hydroxy-2-ethyl4-pyrone.

9. The pharmaceutical composition of claim 8, wherein the hydroxypyrone is 3-hydroxy-2-methyl-4-pyrone.

10. The pharmaceutical composition of claim 8, wherein the hydroxypyrone is 3-hydroxy-2-ethyl-4-pyrone.

11. The pharmaceutical composition of claim 7, wherein the carrier is selected from the group consisting of lactose, starch and dextrin.

* * * * *

UNITED STATES PATENT AND TRADEMARK OFFICE
CERTIFICATE OF CORRECTION

PATENT NO. : 6,048,851
DATED : April 11, 2000
INVENTOR(S) : Lawrence Richard Bernstein It is certified that error appears in the above-indentified patent and that said Letters Patent is hereby corrected as shown below:

In column 1, lines 21-44 should be deleted.

Signed and Sealed this

Thirteenth Day of March, 2001

*Attest:*

NICHOLAS P. GODICI

*Attesting Officer*     Acting Director of the United States Patent and Trademark Office

UNITED STATES PATENT AND TRADEMARK OFFICE
CERTIFICATE OF CORRECTION

PATENT NO.   : 6,048,851
DATED        : April 11, 2000
INVENTOR(S)  : Lawrence R. Bernstein It is certified that error appears in the above-identified patent and that said Letters Patent is hereby corrected as shown below:

Columns 1-16 should be deleted and insert the attached Columns 1-16.

Signed and Sealed this

Twentieth Day of December, 2005

JON W. DUDAS
*Director of the United States Patent and Trademark Office*

SOLID PHARMACEUTICAL COMPOSITIONS FOR THE ORAL ADMINISTRATION OF GALLIUM

CROSS-REFERENCE TO RELATED APPLICATIONS

This is a divisional of U.S. Ser. No. 08/956,175; filed Oct. 22, 1997, allowed, which was a continuation of U.S. Ser. No. 08/655,220, filed Jun. 5, 1996, abandoned which was a continuation of U.S. Ser. No. 08/505,037, filed Jul. 21, 1995, now issued as U.S. Pat. No. 5,574,027, which was a continuation of U.S. Ser. No. 08/309,624, filed Sep. 21, 1994, abandoned, which was a continuation of U.S. Ser. No. 08/104,623, filed Aug. 11, 1993, abandoned, which was a continuation of Ser. No. 07/782,434, filed Oct. 25, 1991, now issued as U.S. Pat. No. 5,258,376, which was a continuation-in-part of U.S. Ser. No. 07/656,016, filed Feb. 14, 1991, abandoned, which was a continuation of Ser. No. 07/440,277, filed Nov. 22, 1989, abandoned.

BACKGROUND OF THE INVENTION

1. Field of the Invention

This invention relates to pharmaceutical gallium compositions, particularly those having enhanced oral bioavailability relative to simple gallium salts and methods for their use. Gallium has demonstrated pharmaceutical value for the treatment of many human and animal disorders, including hypercalcemia, cancer, and especially certain widespread degenerative or metabolic bone diseases such as osteoporosis and Paget's disease.

2. References

The following references are cited in this application as superscript numbers at the relevant portion of the application:

1. Hart and Adamson, Proceedings of the National Academy of Sciences, U.S.A., 68:1623–1626 (1971)
2. Collery, U.S. Pat. No. 4,596,710
3. Adamson et al., Chemotherapy Reports, 59:599–610 (1975)
4. Warrell, Jr. et al., U.S. Pat. No. 4,529,593
5. Bockman et al., U.S. Pat. No. 4,704,277
6. Warrell, Jr. et al., "Gallium in the Treatment of Hypercalcemia and Bone Metastasis", in "Important Advances in Oncology 1989", DeVita, Jr., Editor, J. P. Lippincott Company, Philadelphia, Pa.
7. Porter, "The Use of Opadry, Coateric, and Surelease in the Aqueous Film Coating of Pharmaceutical Oral Dosage Forms", at pp. 317–362 of "Aqueous Polymeric Coatings for Pharmaceutical Dosage Forms", McGinity, Editor, Marcel Decker, Inc., New York, N.Y. (1989)
8. Nagai et al., "Applications of HPMC and HPMCAS Aqueous Film Coatings of Pharmaceutical Dosage Forms", at pp. 81–152 of "Aqueous Polymeric Coatings for Pharmaceutical Dosage Forms", McGinity, Editor, Marcel Decker, Inc., New York, N.Y. (1989)
9. Jones, "Production of Enteric Coated Capsules", Manufacturing Chemist & Aerosol News, 41:43–57 (1970)
10. Messora, U.S. Pat. No. 3,927,195
11. Porter, "Coating of Pharmaceutical Dosage Forms", at Chapter 91, pp. 1633–1643, of "Remington's Pharmaceutical Sciences", Gennaro et al., Editors, 17th Ed. (1985)
12. Windholz et al., The Merck Index, 9th Edition, pp. 741–742, Merck & Company, Rahway, N.J. (1976)
13. Foster et al., "Gallium Nitrate: The Second Metal With Clinical Activity", Cancer Treatment Reports, 70:1311–1319 (1986)
14. Hider et al., U.S. Pat. No. 4,575,502
15. Finnegan et al., Inorganic Chemistry, 26:2171–2176 (1987)
16. Farrar et al., Food and Chemical Toxicology, 26:523–525 (1988)
17. Ott, International Journal of Artifical Organs, 6:173–175 (1983)

The disclosures of each of these references are incorporated herein by reference in their entirety.

3. State of the Art

Gallium is known to accumulate in certain tumors, inflamed tissue, and bone tissue by mechanisms that are largely unknown. Binding of gallium to transferrins, particularly lactoferrin, is thought to be responsible for some of the transport of gallium in the body, and for the concentration or gallium in certain tumors and inflamed tissues. Radioactive $^{67}Ga$ citrate compositions are used in patients to diagnose certain malignancies and infections, including those in bone tissue. Non-radioactive gallium compositions, and compositions containing other Group IIIa elements, have been found effective in treating some tumors in animals and humans. Gallium is thought to be the most effective of these Group IIIa elements[1,3,4]. The art recognizes that gallium is useful for the treatment and prevention of many human and other mammalian diseases, including hypercalcemia, cancer, and certain degenerative or metabolic bone diseases such as osteoporosis and Paget's disease[2-6,13]. Gallium itself appears to be the active agent; the form in which the gallium is administered (e.g. as the nitrate, sulfate, or chloride) does not appear to affect its activity to any significant extent[3,6].

Gallium is particularly useful in the treatment and prevention of hypercalcemia and certain bone diseases. Treatable bone diseases include such widespread conditions as osteoporosis, osteopenia, Paget's disease, malignant bone disease, bone degeneration due to hyperparathyroidism, and other conditions associated with increased bone resorption or turnover in humans or animals[4,6]. In addition to the above, it has been found that gallium increases calcium accretion in bone and decreases bone resorption[5].

Specifically, Warrell et al.[4,6] and Bockman et al.[5] disclose treatments using gallium salts, preferably gallium nitrate, for regulating the resorption of calcium from bone in certain bone diseases and hypercalcemia, and for increasing the mass and tensile strength of bone. Warrell et al.[4] discloses that such regulation entails the generation of plasma gallium concentrations in the patient of from about 0.9 to 2.0 µg/ml whereas Bockman et al.[5] recite the generation of plasma gallium concentrations in the patient of from about 0.1 to 5.0 µg/ml.

Treatment of cancer with gallium nitrate is disclosed in Foster et al.[13] which teaches the administration (by infusion) of gallium nitrate at 700–750 mg/m² by short infusion every 2–3 weeks; 300 mg/m²/day by short infusion for three consecutive days, to be repeated every 2 weeks; and 300 mg/m²/day by continuous infusion for 7 consecutive days, to be repeated every 3–5 weeks. Specific cancers treated in this reference include, by way of example, refractory lymphomas, small cell lung carcinoma, genitourinary malignancies (renal, bladder, prostate, testicular), and multiple myeloma.

On the other hand, Collery[2] discloses the treatment of cancer by the oral administration of a dose of from 200 mg to 1 gram of gallium chloride per day for at least 2 months.

However, in spite of its established utility, the use of gallium in the treatment of such diseases is hampered by the fact that ionic gallium lacks high bioavailability when delivered orally. In fact, ionic gallium is a form of gallium which is poorly absorbed by the gastrointestinal tract. In this regard, Warrell et al.[4] disclose that when a composition of gallium nitrate is administered orally to a dog, only 0.5 to 2% of the gallium is absorbed from the gastrointestinal tract, into the bloodstream and then excreted into the urine. The percent absorption of other $Ga^{+3}$ salts is not likely to be significantly different, as such salts dissociate in aqueous solutions to produce mainly trivalent gallium ions in a similar manner to gallium nitrate.

The low bioavailability of orally delivered gallium salts (i.e., ionic gallium) and the need to generate blood plasma gallium concentrations in the patient of from 0.1 to 5 μg/al of plasma gallium concentration (and preferably 0.5 to 2 μg/ml) for the treatment of hypercalcemia or excessive bone resorption[5] requires that either impractically large doses of orally delivered gallium be administered to the patient or that the gallium be administered via non-oral means (e.g., intravenous delivery). The oral delivery of such gallium salts is not believed to be practical particularly with widespread, chronic conditions such as osteoporosis and the like.

The present invention is directed to the discovery that gallium bioavailability via oral administration is greatly enhanced by using electrostatically neutral gallium chelates of certain 3-hydroxy-4-pyrones. The present invention is directed to the further discoveries that because such neutral gallium chelates decompose in the acidic conditions commonly present in the stomach, pharmaceutical compositions of orally delivered neutral gallium chelates must contain means to inhibit dissociation of the neutral gallium chelates under such acidic conditions.

In regard to the above, it is noted that Finnegan et al.[15] disclose the preparation of aluminum and gallium complexes of some 3-hydroxy-4-pyrones, including maltol. This reference recites that the aluminum maltol complex is highly neurotoxic when injected intracranially into rabbits, and suggests further neurotoxicity experiments with the aluminum and gallium complexes. This reference further recites nuclear magnetic resonance spectroscopy (NMR) experiments that demonstrated significant differences between the aqueous behavior of the complexes of aluminum and gallium, i.e., experiments to determine the stability of gallium complexes as a function of pH could not be performed, whereas such experiments were readily performed on aluminum complexes.

Further regarding the significant differences between aluminum and gallium, aluminum is well known in the art to be a cause of degenerative bone disease[17] as well as being neurotoxic. Contrarily and as previously discussed, gallium is known in the art as effective in the treatment of degenerative bone disease and has shown no reported evidence of neurotoxicity.

Farrar et al.[16] discloses the preparation of an aqueous solution containing 10 mM maltol, 1 mM $Ga(NO_3)_3$, and a trace of $GaCl_3$ labelled with radioactive $^{67}Ga$ for administration to rats by oral gavage. However, it is not established in this reference that this solution contains a significant amount of the neutral 3:1 complex. In any event, Farrar et al. completely fail to even consider the possibility that pH might affect the stability of a Ga-maltol complex. This reference also completely fails to realize, suggest, or imply any method to increase gallium absorption in fed animals. Additionally, this reference fails to suggest combining such gallium complexes with means to inhibit dissociation of the complex in a mammalian stomach.

Lastly, Hider et al.[14] disclose orally deliverable pharmaceutical compositions containing neutral iron complexes of 3-hydroxy-4-pyrones and means to inhibit dissociation of such complexes under acidic conditions. However, the teachings of this reference are expressly limited to iron and it is art recognized that gallium is not equivalent to iron. Further in this regard, iron is a Group VIII metal that is easily oxidized and reduced between its +2 and +3 valences at physiologic conditions, whereas gallium is a Group IIIa semi-metal that exists only with a +3 valence state at physiologic conditions.

SUMMARY OF THE INVENTION

In view of the above, the present invention is directed to methods for increasing the bioavailability of gallium into the bloodstream as well as to pharmaceutical compositions employed to achieve such methods.

In one of its method aspects, the present invention is directed to a method for administering gallium to a mammalian patient (e.g., human patient) which comprises the oral ingestion of a sufficient amount of a pharmaceutical composition comprising (a) a neutral 3:1 gallium complex of a 3-hydroxy-4-pyrone wherein said 3-hydroxy-4-pyrone has the formula

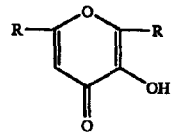

wherein each R is independently selected from the group consisting of hydrogen and alkyl of from 1 to 6 carbon atoms; and (b) means to inhibit dissociation of said complex under acidic conditions of the gastro portion of said gastrointestinal tract so as to provide a blood plasma gallium concentration of from about 0.1 to about 5 μg/ml.

In another method aspect, the present invention is directed to a method for increasing calcium accretion in bone or for decreasing calcium resorption in a mammal (e.g., a human), said method comprising orally administering an effective amount of a gallium composition to increase calcium accretion or decrease bone resorption in a mammal in need of such treatment, said gallium composition being a pharmaceutical composition comprising (a) a neutral 3:1 gallium complex of a 3-hydroxy-4-pyrone wherein said 3-hydroxy-4-pyrone has the formula

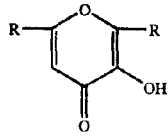

wherein each R is independently selected from the group consisting of hydrogen, and alkyl of from 1 to 6 carbon atoms; and (b) means to inhibit dissociation of said complex under acidic conditions of the gastro portion of said gastrointestinal tract.

In still another method aspect, the present invention is directed to a method for administering gallium to a mammalian patient wherein said administration is by the oral ingestion of a pharmaceutical composition comprising gallium so as to introduce gallium into the gastro-intestinal tract of said patient whereupon gallium is absorbed into the bloodstream of said patient wherein the improvement comprises:

employing in said composition a neutral 3:1 gallium complex of a 3-hydroxy-4-pyrone wherein said 3-hydroxy-4-pyrone has the formula:

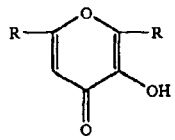

wherein each R is selected from the group consisting of hydrogen, and alkyl of from 1 to 6 carbon atoms; and further employing in said composition means to inhibit dissociation of said complex under acidic conditions of the gastro portion of said gastrointestinal tract.

In one of its composition aspects, the present invention is directed to a pharmaceutical composition comprising (a) a neutral 3:1 gallium complex of a 3-hydroxy-4-pyrone wherein said 3-hydroxy-4-pyrone has the formula:

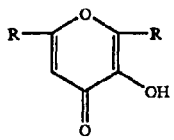

wherein each R is independently selected from the group consisting of hydrogen, and alkyl of from 1 to 6 carbon atoms; and (b) means to inhibit dissociation of said complex under acidic conditions of the gastro portion of said gastrointestinal tract.

The compositions and methods of this invention are useful for orally delivering gallium to humans and other mammals for a wide variety of medical and veterinary applications, including, by way of example, the treatment of bone diseases relating to the increased resorption of calcium into the bloodstream.

DETAILED DESCRIPTION OF THE INVENTION

As noted above, the present invention is directed to methods and compositions for enhancing the bioavailability of gallium from orally delivered pharmaceutical compositions containing gallium. However, prior to discussing this invention in further detail, the following terms will first be defined. Unless defined below, the terms used herein have their normally accepted meanings.

1. Definitions

As used herein, the following terms have the definitions given below:

The term "neutral 3:1 gallium complex of a 3-hydroxy-4-pyrone" refers to an electrostatically neutral complex of $Ga^{+3}$ and 3 equivalents of the anionic form of 3-hydroxy-4-pyrone which complex is represented by the formula $[Ga^{+3}(py^{-1})_3]$ wherein $py^{-1}$ represents the anionic form of 3-hydroxy-4-pyrone which is defined below. Because such complexes do not dissociate to any significant extent in aqueous solutions maintained at a pH of from about 5 to about 9, these complexes remain predominantly electrostatically neutral in such solutions.

In this regard, these complexes are deemed "electrostatically neutral" because there are equal numbers of positive and negative charges in the complex.

Also, it is apparent that the anionic form of the 3-hydroxy-4-pyrone acts as a chelating agent to the gallium and as such, the complex is sometimes referred to herein as "neutral gallium chelates of 3-hydroxy-4-pyrones". It being understood that this latter term is synonymous with the term "neutral 3:1 gallium complex of a 3-hydroxy-4-pyrone".

The term "a 3-hydroxy-4-pyrone" refers to a compound of the Formula 1:

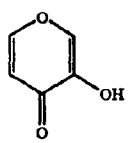

wherein from none to three of the hydrogen atoms attached to the ring carbon atoms are replaced by a hydrocarbon group of from one through six carbon atoms.

Specific compounds encompassed by the term "a 3-hydroxy-4-pyrone" are represented by the Formulas 2–5 below:

Formula 2:

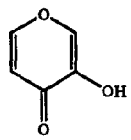

Formula 3:

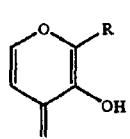

Formula 4:

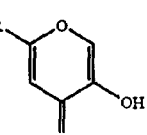

Formula 5:

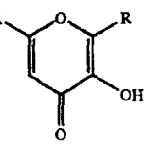

wherein each R is independently a hydrocarbon of from 1 to 6 carbon atoms.

The unsubstituted form of 3-hydroxy-4-pyrone (Formula 2, also called pyromeconic acid) contains three hydrogen atoms that are bound only to ring carbon atoms. As noted above, any combination of these three hydrogen atoms can be substituted with a hydrocarbon group and all possible combinations of such substitutions are encompassed within this invention. The locations of a few possible substitutions are presented in Formulas 3–5, in which R is a hydrocarbon group (including methyl, ethyl, isopropyl, and n-propyl). The hydrocarbon groups are preferably acyclic and are preferably unbranched. Groups containing six or fewer carbon atoms, particularly of one through three carbon atoms, especially methyl or ethyl, are preferred. Single substitution is preferred; a substitution at either the 6-position or especially the 2-position is preferred. Some examples of specific compounds whose gallium complexes may be used in compositions comprised by the invention are: 3-hydroxy-2-methyl-4-pyrone (Formula 3, $R=CH_3$—sometimes referred to as maltol or larixinic acid) and 3-hydroxy-2-ethyl-4-pyrone (Formula 3, $R=C_2H_5$—sometimes referred to as ethyl maltol or ethylpyromeconic acid), both of which are preferred for use in this invention, especially 3-hydroxy-2-methyl-4-pyrone. Other preferred compounds include 3-hydroxy-4-pyrone (Formula 2—sometimes referred to as pyromeconic acid); and 3-hydroxy-6-methyl-4-pyrone (Formula 4, $R=CH_3$).

The term "an anion of a 3-hydroxy-4-pyrone" refers to a compound defined in Formulas 2–5 above wherein the hydroxyl proton has been removed so as to provide for the anionically charged form of these compounds.

The terms "oral administration" and "oral ingestion" refer to all conventional forms for the oral delivery of a pharmaceutical composition to a patient (e.g., human) and that result in the deposition of the pharmaceutical composition into the gastrointestinal tract (including the gastro portion of the gastrointestinal tract, i.e., the stomach) of the patient. Accordingly, oral administration and oral ingestion include, by way of example, actual ingestion of a solid or liquid pharmaceutical composition, oral gavage, and the like.

The term "inhibit dissociation" means that at least 20%, preferably at least 50% and more preferably at least 80%, of the complex is not dissociated under acidic conditions (e.g., about pH 2–4) for a period of at least 1 hr and preferably at least 3 hours.

2. Synthesis and Methodology

This invention includes methods for the preparation of neutral 3:1 gallium complexes of 3-hydroxy-4-pyrone or 3-hydroxy-4-pyrones wherein from one through three of the hydrogen atoms attached to ring carbon atoms are replaced by a hydrocarbon group containing from one through six carbon atoms. Such methods comprise reacting such hydroxypyrones with gallium ions and isolating, at least in part, the resulting complex or complexes.

Specifically, the neutral 3:1 gallium complex of a 3-hydroxy4-pyrone is prepared by the reaction of gallium ions and the 3-hydroxy-4-pyrones in solution. Gallium ions can be derived from a gallium salt, such as a gallium halide, particularly gallium chloride, or a gallium nitrate compound, especially a hydrated gallium nitrate. The gallium nitrate compounds are often preferable as they are easier to work with than gallium halides, which may be highly irritating and may react violently with many solvents, including water. Using the proper safeguards, a variety of gallium salts can be used. The reaction is conveniently effected in a mutual solvent, including but not limited to mixtures containing water, ethanol, methanol, and chloroform. Pure water may be used in many cases, though the purification of the gallium hydroxypyrone complexes may be difficult if it is used. A preferable method, if it is desired to separate at least a major part of reaction by-products such as sodium nitrates, sodium chloride, and sodium carbonates, is to use a mixture containing roughly equal parts of ethanol and chloroform, with a trace of water. The reaction by-products mentioned above have very low solubilities in this mixture and can be removed readily by filtration.

To produce the preferred neutral 3:1 hydroxypyrone:gallium complex, the hydroxypyrone and the gallium ions are mixed in 3:1 molar proportions, preferably with a slight excess of hydroxypyrone to insure a great preponderance of the 3:1 complex over the 2:1 and 1:1 complexes. The proportions of the particular complexes formed are dependent upon the pH of the solution. When a gallium salt such as a halide or nitrate is dissolved, the resulting solution will generally have a low pH. To form a preponderance of the preferred neutral 3:1 complex, a pH of from 5 to 9, preferably 7 through 8, is used. If a more acidic solution is used, a preponderance of the less preferred 2:1 and 1:1 complexes may instead be formed, even if a large excess of hydroxypyrone is present. Under highly basic conditions, poorly soluble gallium hydroxides may precipitate. It is preferable to regulate the pH with materials other than hydroxides such as sodium hydroxide, as the use of such hydroxides may cause the precipitation of poorly soluble gallium hydroxides, which are not wanted, and the pH may actually be buffered at a low level by this precipitation. The use of a carbonate, especially sodium carbonate, is preferred to regulate the pH. The use of sodium carbonate in a solvent mixture containing ethanol and chloroform, for example, can result in the precipitation of sodium nitrates that are very slightly soluble in this mixture, and which can be filtered off if desired to help purify the solution containing the desired pharmaceutical compositions.

The reaction to form the hydroxypyrone-gallium complex in solution is generally complete within about five minutes at about 20° C. Gentle stirring or other agitation of the solution promotes a uniform, rapid reaction. Longer reaction times may be used if found necessary. Following the separation, if desired, of reaction by-products such as sodium nitrates, sodium chloride, and sodium carbonates (depending on the solvents and reactants used), the reaction mixture may be evaporated slowly in air or, more rapidly, through the use of a rotary evaporator or by freeze drying, as examples. After drying, the gallium complex or complexes will remain in solid form. Recrystallization can be accomplished, if desired, using a suitable solvent, including but not limited to chloroform, alcohols such as ethanol and methanol, ether, water, acetone, and mixtures containing such solvents. Suitable solvents will depend upon which particular gallium complex(es) and impurities are present, upon the impurities to be separated, and upon the temperature and other physical conditions.

It is noted that the mentioned methods are not the only ones that can produce hydroxypyrones and gallium complexes with hydroxypyrones and that various alternative methods may be used as will be apparent to those skilled in the art. Additionally, in preparing the neutral 3:1 complexes of gallium with 3-hydroxy-4-pyrone, a single 3-hydroxy-4-pyrone or a mixture of 3-hydroxy-4-pyrones can be used. However, preferably, only a single 3-hydroxy-4-pyrone is employed.

With regard to the preparation of 3-hydroxy-4-pyrones which are used as starting materials in the preparation of the neutral 3:1 complexes of gallium with 3-hydroxy-4-pyrones, certain of these compounds occur naturally and may be obtained by extraction from the natural sources. For example, maltol is found in the bark of the young larch tree (*Larix decidua* Mill.), and in pine needles, chicory, wood tars and oils, and roasted malt[12]. Certain of the 3-hydroxy-4-pyrones are available commercially, including maltol and ethyl maltol. Others can be made from pyromeconic acid as a starting material, which can be derived from the decarboxylation of meconic acid. Methods for preparing such other 3-hydroxy-4-pyrones are well known in the art. Additionally, it is noted that maltol and ethyl maltol are in widespread use as flavoring and fragrance-enhancing agents for foods, and have very low toxicities when taken orally.

3. Pharmaceutical Compositions

The methods of this invention are achieved by using a pharmaceutical composition comprising a neutral 3:1 complex of gallium with 3-hydroxy-4-pyrone and means to inhibit dissociation of said complex under acidic conditions in the gastro (stomach) portion of the gastrointestinal tract.

As noted above, this invention is directed in part to the discovery that while the neutral 3:1 complex of gallium with 3-hydroxy-4-pyrones delivers gallium to the bloodstream from the gastrointestinal tract, this complex will dissociate under acidic conditions (generally at a pH of about 4 or less) such as those which can be present in the stomach to the less absorbable 2:1 and 1:1 complexes, together with free hydroxypyrone and ionic gallium. Accordingly, in order to maintain the orally delivered gallium in a form which is highly absorbable in the gastrointestinal tract, the pharmaceutical compositions of this invention are formulated to contain a means to inhibit dissociation of this complex when exposed to the acidic conditions of the stomach.

Means to inhibit or prevent dissociation of this complex when exposed to the acidic conditions of the stomach include the following preferred methods:

(1) Addition of a sufficient amount of a pharmaceutically compatible buffering agent to the 3:1 complex that would bring the pH of the stomach fluids to a range of from about 5–9 and preferably from about 6–7 so that the stomach fluids would no longer disrupt the 3:1 hydroxypyrone:Ga complex.

Pharmaceutically compatible buffering agents are those which, while acting as a buffering agent, do not significantly alter the ability of the neutral 3:1 gallium complex to deliver gallium to the bloodstream of the patient and are not toxic either alone or in combination with the neutral gallium complex. The particular pharmaceutically compatible buffering agent employed is not critical. Examples of preferred pharmaceutically compatible buffering agents include, by way of example, calcium carbonate ($CaCO_3$), sodium bicarbonate ($NaHCO_3$) and the like. On the other hand, aluminum hydroxide, $Al(OH)_3$, and other aluminum-containing compounds, by way of example, should be avoided. Other pharmaceutically compatible buffering agents are well known in the art and are recited in standard pharmaceutical manufacturing textbooks (e.g., Remington's Pharmaceutical Sciences by Mack Publishing Company).

(2) Adding to the pharmaceutical composition containing the 3:1 complex an excess of free hydroxypyrone (or a salt thereof containing a physiologically acceptable cation), particularly the one used to make the 3:1 complex. Such a mixture, when dissolved in the stomach, has the effect of shifting the equilibrium among the 1:1, 2:1, and 3:1 complexes towards a preponderance of the 3:1 complex. In this embodiment, the weight of the free hydroxypyrone incorporated into the formulation is preferably 0.1 to 100 times the weight of the 3:1 complex employed in the formulation, and more preferably 0.1 to 10 times. This method, by itself, is not highly preferred but may be used in conjunction with other methods to inhibit dissociation.

(3) Formulating the pharmaceutical composition that contains the 3:1 complex in delayed release form, so that a preponderance of the complex is not released until the intestinal tract is reached. An example of such a composition is to formulate the 3:1 complex with certain gels, preferably hydrogels such as a polymerized polyethylene glycol hydrogel, that adsorb the 3:1 complex and then release it after ingestion only very slowly while in the stomach. The preparation of such delayed release formulations, particularly those using hydrogels, is well known in the art.

(4) Most preferably, formulating or packaging the 3:1 complex in such a way that the release of the 3:1 complex is prevented or inhibited until the basic, or less acidic, conditions of the intestinal tract are reached. Specific preferred methods include:

(a) Encapsulating the 3:1 complex in a material that is resistant to dissolution until the intestinal tract is reached, most preferably using a tablet or capsule that is enteric coated, or granules that are enteric coated, to inhibit or prevent release of the 3:1 complex until a pH greater than about 5 or 6 is reached. Enteric coating of tablets, capsules, and granules is well known in the art.

(b) Microencapsulating the 3:1 complex within liposomes, preferably made from phospholipids, that do not dissociate under the acidic conditions of the stomach, but that will release the 3:1 complex in the higher pH conditions of the intestinal tract. Such liposomes are also well known in the art.

The most preferred method, enteric coating tablets, granules or especially capsules, is well known in the art. Such methods are described, for example, by Porter[7], by Nagai et al.[8], by Jones[9], by Messora[10], and by Porter[11], which are incorporated herein by reference in their entirety. Preferred materials for the enteric coating include, by way of example, cellulose acetate phthalate, hydroxypropyl methylcellulose phthalate, poly(vinyl acetate phthalate), hydroxypropyl methylcellulose acetate succinates, poly(meth)acrylates, and, preferably, cellulose acetate phthalate/diethylphthalate. When capsules are coated, a plasticizer should be used (such as hydroxypropyl methylcellulose acetate succinates/triethyl citrate or especially cellulose acetate phthalate/diethylphthalate) to minimize brittleness in the coating and to inhibit cracking of the coating. Tablets and granules can also be used.

In addition to the above, two or more means to inhibit dissociation of these complexes can be employed in combination so as to enhance the level of inhibition, i.e., a pharmaceutically compatible buffer can be employed in combination with an excess of free 3-hydroxy-4-pyrone.

When used for oral administration, which is preferred, the gallium complex may be formulated in a variety of ways. It will preferably be in solid form, and may optionally and conveniently be used in compositions containing a pharmaceutically inert carrier including conventional solid carriers such as lactose, starch, or dextrin, which are conveniently presented in tablet or capsule form. Materials and methods to enhance gallium absorption, including those mentioned in the preceding paragraph, may be incorporated; the use of enteric coated tablets or capsules, as previously discussed, is preferred. In this regard, the complex itself, with or without additional hydroxypyrone, buffers, or other active ingredients, may also be used without the addition of inert pharmaceutical carriers, particularly for use in capsule form. In this embodiment, the capsule serves as the means to inhibit dissociation of the complex.

Compositions including a liquid pharmaceutically inert carrier (e.g., water) may also be considered for oral administration that comprise an appropriate means for inhibiting dissociation of the 3:1 complex in the acidic conditions of the stomach, preferably through the use of a pharmaceutically compatible buffer, preferably $CaCO_3$ or $NaHCO_3$. The use of such buffers is well known in the art.

Doses are selected to provide pharmaceutically active plasma gallium concentrations for the treatment of excessive resorption of calcium from bone (e.g., arising from hypercalcemia, osteoporosis, osteopenia, Paget's disease or cancer), which are established to be about 0.1–5.0 µg/ml, preferably about 0.9–2.0 µg/ml[4,5]. To obtain such physiologically active gallium levels in the patient, compositions for oral administration provide about 0.1–200 mg/m$^2$/day gallium (delivered as a 3:1 complex with hydroxypyrone in the composition) and preferably about 1–30 mg/m$^2$/day.

For the 3:1 complexes containing maltol or ethyl maltol, this corresponds to a daily dose, preferably given in unit dose form, of about 0.9–1800 mg of the complex for a 50 kg individual, preferably about 9–360 mg. The compositions, when formulated according to the preferred methods described above, may be effectively administered at any time, though preferably two or more hours after meals.

The pharmaceutical compositions described herein generally comprise from about 1 to about 99 weight percent of a neutral 3:1 complex of gallium with 3-hydroxy-4-pyrone. Preferably, when an inert pharmaceutical carrier is employed in the compositions of this invention, the compositions contain from about 1 to about 99 weight percent of the pharmaceutically inert carrier. The compositions also contain a sufficient amount of a means to inhibit dissociation of the complex under the acidic conditions of the stomach. Preferably, when such means include a buffer or an excess of hydroxypyrones, the composition comprising such means is incorporated into the pharmaceutical composition at no more than about 98 weight percent of the composition.

Formulations may also be considered for other modes of administration, for example per rectum, transdermally, and by intravenous, subcutaneous, and intramuscular injection. These formulations may contain a liquid carrier that may be oily, aqueous, emulsified, or contain certain solvents suitable to the mode of administration. Compositions may be formulated in unit dose form, which is preferred, or in multiple or sub-unit doses.

Formulations may also be produced that contain active ingredients other than the gallium complexes. These may include other agents to regulate calcium resorption from bone, for example, but other active agents may also be incorporated.

When treating cancer, established doses for gallium nitrate delivery are from 300 mg/m$^2$/day to 700 mg/m$^2$/day[13] which can be extrapolated for the administration of a 3:1 neutral complex of 3-hydroxy-4-pyrone and gallium.

4. Utility

As noted previously, the art recognizes that gallium is useful in treating conditions such as hypercalcemia, cancer [e.g., refractory lymphomas, small cell lung carcinoma, genitourinary malignancies (renal, bladder, prostate, testicular), multiple myeloma, and the like] and degenerative bone diseases. For example, the art recognizes that blood plasma levels of from about 0.1 to about 5 μg/ml are effective in treating hypercalcemia; for treating other degenerative bone diseases; and for increasing the mass and tensile strength of bone[5].

The compositions and methods of this invention are useful in providing enhanced bioavailability of gallium to the patient's bloodstream as compared to the bioavailability of gallium achieved with gallium salt compositions heretofore employed. Accordingly, on equal weight of gallium basis, pharmaceutical compositions containing a complex of this invention together with means to prevent dissociation of the complex in the patient's stomach deliver significantly greater quantities of gallium to the bloodstream of a patient as compared to the amount of gallium delivered to the bloodstream by pharmaceutical compositions containing prior art gallium salts. Such enhanced delivery of gallium by pharmaceutical compositions containing neutral 3:1 gallium complexes permit the use of less gallium per unit dose as compared to pharmaceutical compositions containing gallium salts while still providing efficacious blood plasma gallium concentrations. The use of less gallium while still achieving the requisite blood plasma gallium concentrations by the compositions of this invention provides a practical method for the oral delivery of gallium. Additionally, because the amount of gallium ingested is reduced, side effects from gallium ingestion are expected to be reduced.

Notwithstanding the fact that gallium is administered as a neutral complex, the present invention is also based on the discovery that gallium is nevertheless transported in vivo into the bloodstream of the patient.

The following examples are offered to illustrate this invention and are not to be construed in any way as limiting the scope of this invention.

In these examples, the following abbreviations have the following meanings:

| | |
|---|---|
| Å = | Ångstrom |
| C = | Centigrade |
| kg = | kilogram |
| M = | Molar |
| mg = | milligram |
| ml = | milliliter |
| mm = | millimeter |
| N = | Normal |
| nm = | nanometers |

Also, in X-ray fluorescence and diffraction data given in Example 1, the numbers in parentheses after the value reported represent the estimated standard deviation in the last digit.

EXAMPLES

Example 1

Preparation of Gallium Ethyl Maltol

A 1.5M solution of ethyl maltol in chloroform is mixed with an equal volume of a 0.5M solution of gallium nitrate nonohydrate in ethanol to provide a 3:1 molar ratio of ethyl maltol to gallium ions in the mixture. The mixture is stirred for 7 minutes at 22° C. Solid anhydrous sodium carbonate is then added in a 10 molar excess, and stirring continues for an additional ten minutes. When the sodium carbonate is added, a trace of water may sometimes need to be added to facilitate the reaction, which is evidenced by some effervescence. The mixture is then filtered and the filtrate evaporated to give the solid 3:1 complex of ethyl maltol and gallium.

The complex as so produced contains 14.3(1) weight percent gallium by x-ray fluorescence analysis, as predicted for $Ga(C_7H_6O_3)_3$. The material forms white to pale beige monoclinic crystals with unit cell parameters of about a=7.899(1) Å, b=8.765(1) Å, c=31.626(2) Å, beta=103.253(7) degrees, V=2131 Å$^3$, based on powder x-ray diffraction analysis. The solubility of this compound is measured as about 5 millimolar in distilled deionized water at 23° C. Crystallization from other solvents or under other conditions may produce other crystal structures. Under some conditions, water may also be incorporated into the structure.

Example 2

Bioavailability Study in Rabbits

A test of the oral bioavailability of the 3:1 ethyl maltol:gallium complex in rabbits was conducted. In this test, the complex was given to rabbits and compared to a solution of gallium nitrate. Six female New Zealand white rabbits weighing between 2.68 and 2.91 kg were used, and were not fed for 18 hours before starting the experiment. A suspension of the 3:1 gallium ethyl maltol complex in double distilled water was prepared with a concentration of 10 mg elemental gallium per 4 ml of suspension. A solution of gallium nitrate nonohydrate dissolved in double distilled water was also prepared, which had a concentration of 10 mg elemental gallium per 4 ml of solution. A small amount of solid sodium carbonate was added to the latter solution to bring the pH up to about 6. Each of the two solutions was given to three rabbits by oral gavage (through a tube inserted through the mouth to the stomach) in the amount of 4 ml per kg of body weight. The stomach tubes were flushed by three ml of water following administration of the solutions.

Six ml of blood was taken from each rabbit at 1 hour, 2 hours, 4 hours, 8 hours, and 24 hours following administration of the solutions, and the serum separated and frozen. Control samples of blood were taken 24 hours earlier. The frozen serum samples were then sent to an independent testing laboratory for determination of the gallium contents by graphite furnace atomic absorption analysis. The testing laboratory received numbered serum samples, and never had any knowledge of the experimental conditions used to produce the samples. The results of the analyses are indicated in Table 1. Due to uncertainties in the analytical procedures for gallium in serum, the relative proportions of gallium in the serum samples are considered more significant than the actual reported concentrations.

It is seen from Table 1 that the gallium ethyl maltol suspension was absorbed in significantly higher amounts than the gallium nitrate suspension of equal volume and gallium concentration. It is important to note that no attempt was made to counteract the adverse effects of the 3:1 gallium ethyl maltol complex being exposed to the acidic conditions of the stomach. This study should therefore be considered to give a minimal value for the oral bioavailability of the gallium ethyl maltol complex compared to gallium nitrate.

TABLE 1

Mean gallium content of rabbit serum (ng/ml).

| | Rabbits treated with | |
|---|---|---|
| | Composition A (3 animals) | Composition B (3 animals) |
| pre-treatment | 0 | 0 |
| 1 hour | 90 | 51 |
| 2 hours | 274 | 99 |
| 4 hours | 260 | 118 |
| 8 hours | 212 | 103 |
| 24 hours | 84 | 64 |

Composition A = Gallium ethyl maltol suspension
Composition B = Gallium nitrate solution Example 3
Preparation of Gallium Maltol Maltol is dissolved in chloroform to form a 0.75M solution, and gallium nitrate nonohydrate is dissolved in ethanol to form a 0.5M solution. To 20 ml of the 0.75M maltol solution in chloroform is slowly added, with continuous stirring, 10 ml of the 0.5M gallium nitrate nonohydrate solution in ethanol. The resulting solution is stirred for 5 minutes at 23° C. About 5.5 grams of powdered anhydrous sodium carbonate are added, and stirring continues for additional 12 minutes. The mixture is filtered to remove all solids, and the filtrate is evaporated in a rotary evaporator. The remaining crystalline solid is the 3:1 maltol:gallium composition. This composition is analyzed using powder x-ray diffraction and found to consist of orthorhombic crystals with unit cell dimensions of about a=18.52(1) Å, b=16.94(1) Å, c=12.02(1) Å. The solubility of this composition is measured as about 24 millimolar in distilled deionized water at 23° C.

The stability of the neutral 3:1 maltol:gallium complex was studied in aqueous solutions at various pH values. The complex was studied at two concentrations in double distilled deionized water: $2.5 \times 10^{-6}$ M and $1.0 \times 10^{-2}$ M. The pH was adjusted by adding either 1N HCl or 1N $Na_2CO_3$. The stability of the complex was determined using ultraviolet spectroscopy over the region 200–450 nm at 25° C. Several absorption peaks are observed in this range, including those at about 212–217 nm, 248 nm, 273 nm, 318 nm, and 385 nm. An isobesic point occurs over much of the pH range at about 290 nm. In the very dilute solutions ($2.5 \times 10^{-6}$ M), the neutral 3:1 complex appears to be stable from about pH 4.5 to 9.5. For the less dilute solutions ($1.0 \times 10^{-2}$ M), the determination was more difficult due to the very high absorbance. The stability region appears very similar to that of the highly dilute solution, possibly slightly wider.

Example 4
Preparation of Enteric Coated Capsule Formulation

The 3:1 maltol:gallium composition is prepared as described in Example 3. Into a standard size 3 hard gelatin capsule (about 15.5 mm long and 5.8 mm diameter) is added 40 mg of the 3:1 maltol:gallium composition, 10 mg of maltol, and about 190 mg of starch. The capsule is closed and is then coated with a layer of cellulose acetate phthalate/diethyl phthalate using a pilot-scale procedure described by Jones[9]. Acetone is used as a solvent, and a coating thickness of about 35 micrometers is obtained. Such a capsule inhibits the release of its contents (the 3:1 maltol:gallium composition) in the acidic conditions of the stomach, but releases its contents in the small intestine, where the pH is greater than about 5.5.

Other materials well known in the art can be used to enteric coat the capsule by merely substituting for the cellulose acetate phthalate/diethyl phthalate employed in Example 4 above. Such other materials include, by way of example, cellulose acetate phthalate, hydroxypropyl methylcellulose phthalate, poly(vinyl acetate phthalate), hydroxypropyl methylcellulose acetate succinates, poly(meth) acrylates, and the like.

Example 5
Preparation of Capsules Containing a Pharmaceutically Acceptable Buffer The purpose of this example is to demonstrate the preparation of an orally deliverable pharmaceutical composition containing a neutral complex of gallium and a 3-hydroxy-4-pyrone wherein the means to inhibit dissociation of the complex in the acidic conditions of the stomach is the use of a pharmaceutically acceptable buffer. Specifically, 40 mg of the 3:1 maltol:gallium composition, from about 50 to about 1000 mg (preferably 500 mg) of calcium carbonate, and the balance starch, are added to a standard gelatin capsule. The capsule is then closed to provide a composition of this invention. Such a capsule will inhibit the dissociation of the 3:1 maltol:gallium composition in the acidic conditions of the stomach by raising the pH of the fluid in the stomach.

In view of the above, other neutral complexes of gallium and 3-hydroxy-4-pyrones could be prepared in the methods described above by merely substituting such other 3-hydroxy-4-pyrones for maltol and for ethyl maltol described in the above examples. Similarly, other means to prevent dissociation of the neutral complex could be employed by merely substituting such other means for the means exemplified above.

Specifically, from about 50 to about 1000 mg of other pharmaceutically acceptable buffers can be employed in place of calcium carbonate in the capsules of Example 5. Such other pharmaceutically acceptably buffers include, by way of example, sodium bicarbonate, sodium carbonate and the like.

What is claimed is:

1. A pharmaceutical composition for oral administration to a human individual, comprising, in a solid dosage form, approximately 0.9 to 1800 mg of a neutral 3:1 hydroxypyrone:gallium complex in which the hydroxypyrone is either unsubstituted or substituted with one to three lower alkyl substituents, a pharmaceutically inert carrier suitable for oral drug administration, and, optionally, an additional active agent.

2. The pharmaceutical composition of claim 1 wherein an additional active agent is present.

3. The pharmaceutical composition of claim 2, wherein the additional active agent is effective to regulate calcium resorption from bone.

4. The pharmaceutical composition of claim 1, comprising approximately 9 to 360 mg of the neutral 3:1 hydroxypyrone:gallium complex.

5. The pharmaceutical composition of claim 2, comprising approximately 9 to 360 mg of the neutral 3:1 hydroxypyrone:gallium complex.

6. The pharmaceutical composition of claim 3, comprising approximately 9 to 360 mg of the neutral 3:1 hydroxypyrone:gallium complex.

7. A pharmaceutical composition for oral administration to a human individual, comprising, in a solid dosage form, approximately 0.9 to 1800 mg of a neutral 3:1 hydroxypyrone:gallium complex in which the hydroxypyrone is selected from the group consisting of 3-hydroxy-4-pyrone, 3-hydroxy-2-methyl-4-pyrone, 3-hydroxy-2ethyl-4-pyrone, and 3-hydroxy-6-methyl-4-pyrone, a pharmaceutically inert carrier suitable for oral drug administration, and an additional active agent effective to regulate calcium resorption from bone.

8. The pharmaceutical composition of claim 7, wherein the hydroxypyrone is selected from the group consisting of 3-hydroxy-2-methyl-4-pyrone and 3-hydroxy-2-ethyl-4-pyrone.

9. The pharmaceutical composition of claim 8, wherein the hydroxypyrone is 3-hydroxy-2-methyl-4-pyrone.

10. The pharmaceutical composition of claim 8, wherein the hydroxypyrone is 3-hydroxy-2-ethyl-4-pyrone.

11. The pharmaceutical composition of claim 7, wherein the carrier is selected from the group consisting of lactose, starch and dextrin.

* * * * *